(12) United States Patent
Motomura et al.

(10) Patent No.: US 7,420,176 B2
(45) Date of Patent: Sep. 2, 2008

(54) SPECT APPARATUS

(75) Inventors: Nobutoku Motomura, Nasushiobara (JP); Hisato Maeda, Toyoake (JP)

(73) Assignee: Fujita Educational Institution, Toyoake-shi (JP)

( * ) Notice: Subject to any disclaimer, the term of this patent is extended or adjusted under 35 U.S.C. 154(b) by 269 days.

(21) Appl. No.: 11/244,283

(22) Filed: Oct. 6, 2005

(65) Prior Publication Data
US 2006/0078082 A1 Apr. 13, 2006

(30) Foreign Application Priority Data
Oct. 7, 2004 (JP) ............................. 2004-295250
Dec. 3, 2004 (JP) ............................. 2004-351724

(51) Int. Cl.
*G21G 4/00* (2006.01)
(52) U.S. Cl. ............. 250/363.04; 250/369; 250/363.09; 250/252.1
(58) Field of Classification Search ................ 378/4; 250/493.1–504 H, 363.09, 363.04, 369, 252.1
See application file for complete search history.

(56) References Cited
U.S. PATENT DOCUMENTS 7,323,689 B2 * 1/2008 Hawman ............... 250/363.04
2002/0130265 A1 * 9/2002 Zerg et al. ............. 250/363.04
2006/0065837 A1 * 3/2006 Hawman ............... 250/363.04
2006/0091315 A1 * 5/2006 Hawman ............... 250/363.04
2007/0217666 A1 * 9/2007 Gal et al. .................... 382/131
2008/0042067 A1 * 2/2008 Rousso et al. .......... 250/363.04
2008/0087833 A1 * 4/2008 McCroskey et al. .... 250/370.08

OTHER PUBLICATIONS

Paul R. Edholm, et al., "Novel Properties of the Fourier Decomposition of the sinogram", Physics and Engineering of Computerized multidimensional Imaging and Processing, SPIE, vol. 671, 1986, pp. 8-18.

* cited by examiner

*Primary Examiner*—Jack I. Berman
*Assistant Examiner*—Andrew Smyth
(74) *Attorney, Agent, or Firm*—Oblon, Spivak, McClelland, Maier & Neustadt, P.C.

(57) ABSTRACT

A SPECT apparatus has a two-dimensional detector that detects radiations from RIs in a patient via a collimator. A correction processing unit corrects plural two-dimensional projection distributions with different projection angles, which are detected by the detector, on a three-dimensional frequency space according to plural correction functions corresponding to plural distances, respectively. Consequently, a fall in spatial resolution having dependency on distances between the respective RIs and the detector is reduced. A reconfiguring unit reconfigures a three-dimensional RI distribution from the plural two-dimensional projection distributions corrected.

14 Claims, 9 Drawing Sheets

TWO-DIMENSIONAL FOURIER TRANSFORMATION OF SINOGRAM $G(\gamma, n)$

SINOGRAM $g(X, \phi)$

COORDINATES OF SPECT

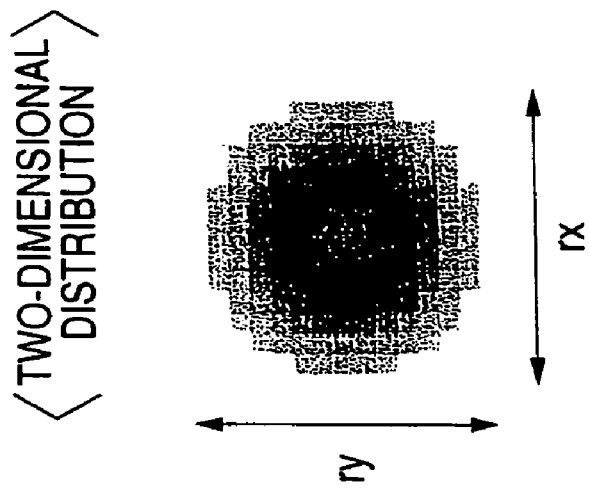
FIG. 7A ⟨ONE-DIMENSIONAL DISTRIBUTION⟩
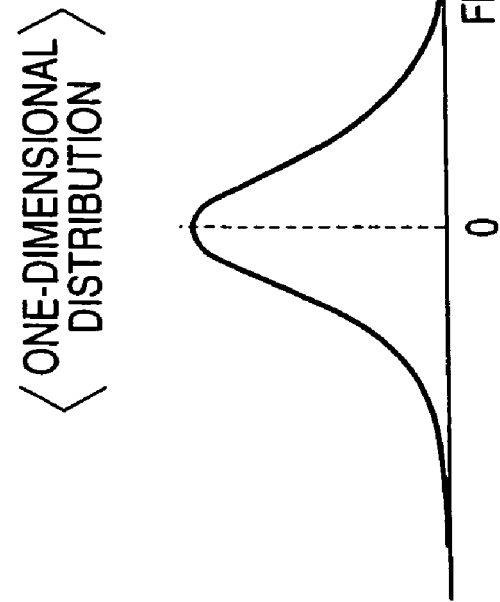
FIG. 7B ⟨TWO-DIMENSIONAL DISTRIBUTION⟩

THREE-DIMENSIONAL SPECT COORDINATE SYSTEM

THREE-DIMENSIONAL SINOGRAM $G(X, \phi, z)$

THREE-DIMENSIONAL FOURIER TRANSFORMATION OF SINOGRAM $G(\gamma, n, w)$

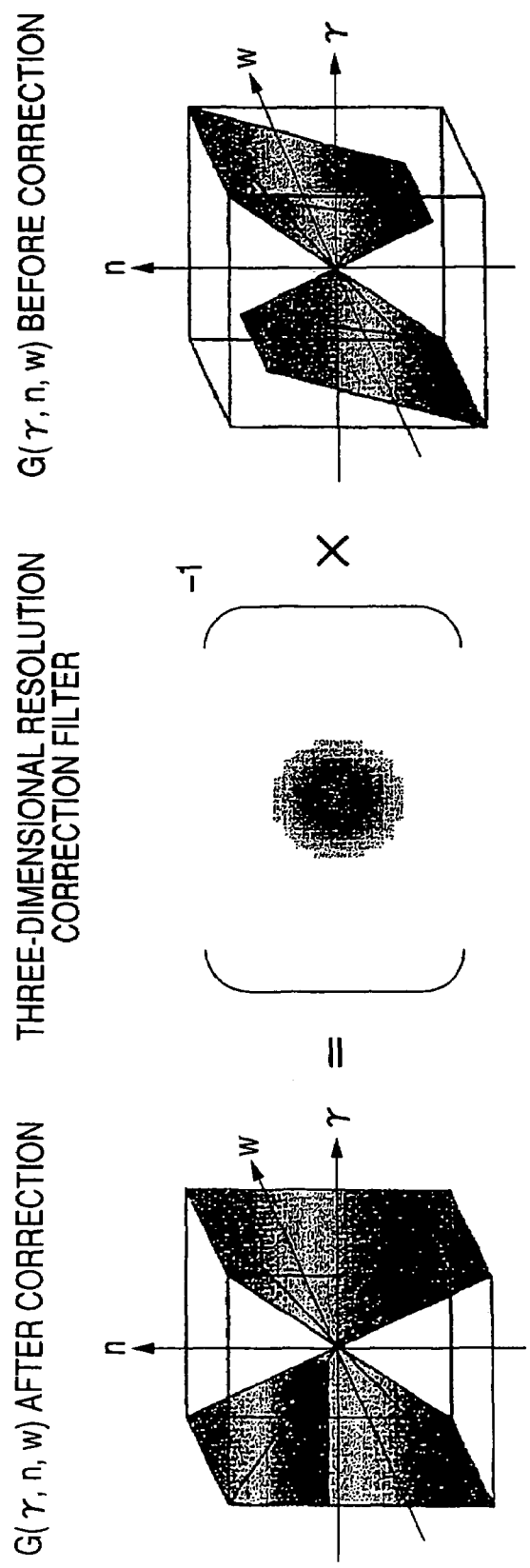

US 7,420,176 B2

SPECT APPARATUS

CROSS-REFERENCE TO RELATED APPLICATIONS

This application is based upon and claims the benefit of priority from prior Japanese Patent Applications No. 2004-295250, filed on Oct. 7, 2004; and No. 2004-351724, filed on Dec. 3, 2004, the entire contents of both of which are incorporated herein by reference.

BACKGROUND OF THE INVENTION

1. Field of the Invention

The present invention relates to a Single Photon Emission CT (SPECT) apparatus.

2. Description of the Related Art

Nuclear medicine is medicine for dosing a drug marked by radioactive isotopes (hereinafter, "RIs") in a patient and imaging an internal RI distribution of the RIs to perform diagnosis. In a nuclear medicine diagnostic apparatus, an apparatus for imaging a three-dimensional distribution of the internal RIs is a Single Photon Emission CT (hereinafter, SPECT) apparatus.

In the SPECT apparatus, filter processing is often applied to collected data of two-dimensional projection distribution to reduce a noise component and correct spatial resolution. It is effective to carry out the filter processing to projection data before reconfiguration.

The filter processing is described in the following document: Edholm P E, Lewitt R M and Lindholm B: Novel properties of the Fourier decomposition of the sinogram. International Workshop on Physics and Engineering of Computerized Multidimensional Imaging and Processing. Proc of SPIE, 671, 8-18, 1986.

One of causes of a fall in spatial resolution is an incidence width of a gamma ray (see FIG. 4). Incidence widths w1 and w2 change according to distances d1 and d2 between a radiation source and a detector. Spatial resolution of a radiation source S2 farther from a detector 3 than a radiation source S1 is lower than that of a radiation source S1.

However, at a stage of the two-dimensional projection distribution data before reconfiguration, since the distances d1 and d2 cannot be separated, it is impossible to effectively correct the spatial resolution.

BRIEF SUMMARY OF THE INVENTION

It is an object of the invention to effectively correct a fall in spatial resolution in a SPECT apparatus.

According to an aspect of the present invention, there is provided a SPECT apparatus including: a two-dimensional detector that detects radiations from RIs in a patient via a collimator; a correction processing unit that corrects plural two-dimensional projection distributions with different projection angles, which are detected by the detector, on a three-dimensional frequency space according to plural correction functions corresponding to plural distances, respectively; and a reconfiguring unit that reconfigures a three-dimensional RI distribution from the plural two-dimensional projection distributions corrected.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out herein after.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 7A is a diagram showing a one-dimensional distribution (a line spread function) of unsharpness in the embodiment;

FIG. 7B is a diagram showing a two-dimensional distribution (a point spread function) of unsharpness in the embodiment;

FIG. 9 is a diagram showing a correction processing for a three-dimensional sinogram in the embodiment.

DETAILED DESCRIPTION OF THE INVENTION

A Single Photon Emission CT (SPECT) apparatus according to an embodiment of the invention will be hereinafter explained with reference to the accompanying drawings. Note that the invention is not limited to the SPECT apparatus. It is possible to provide the invention as a method for data processing including data correction and image reconfiguration processing in the SPECT apparatus and a program for causing a computer to realize the method.

Figure 1:
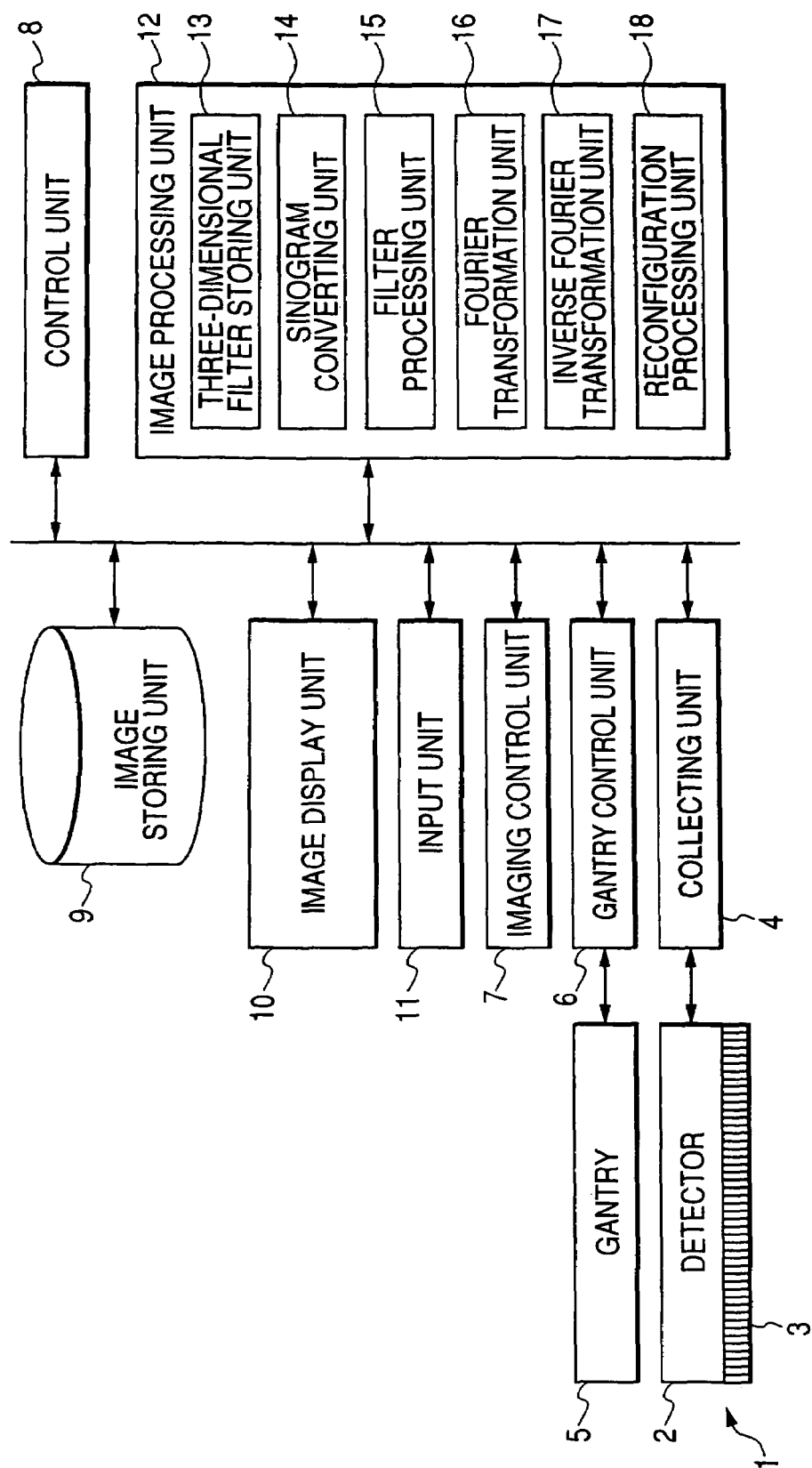
FIG. 1 is a diagram of a SPECT apparatus according to an embodiment of the invention.
Figure 2:
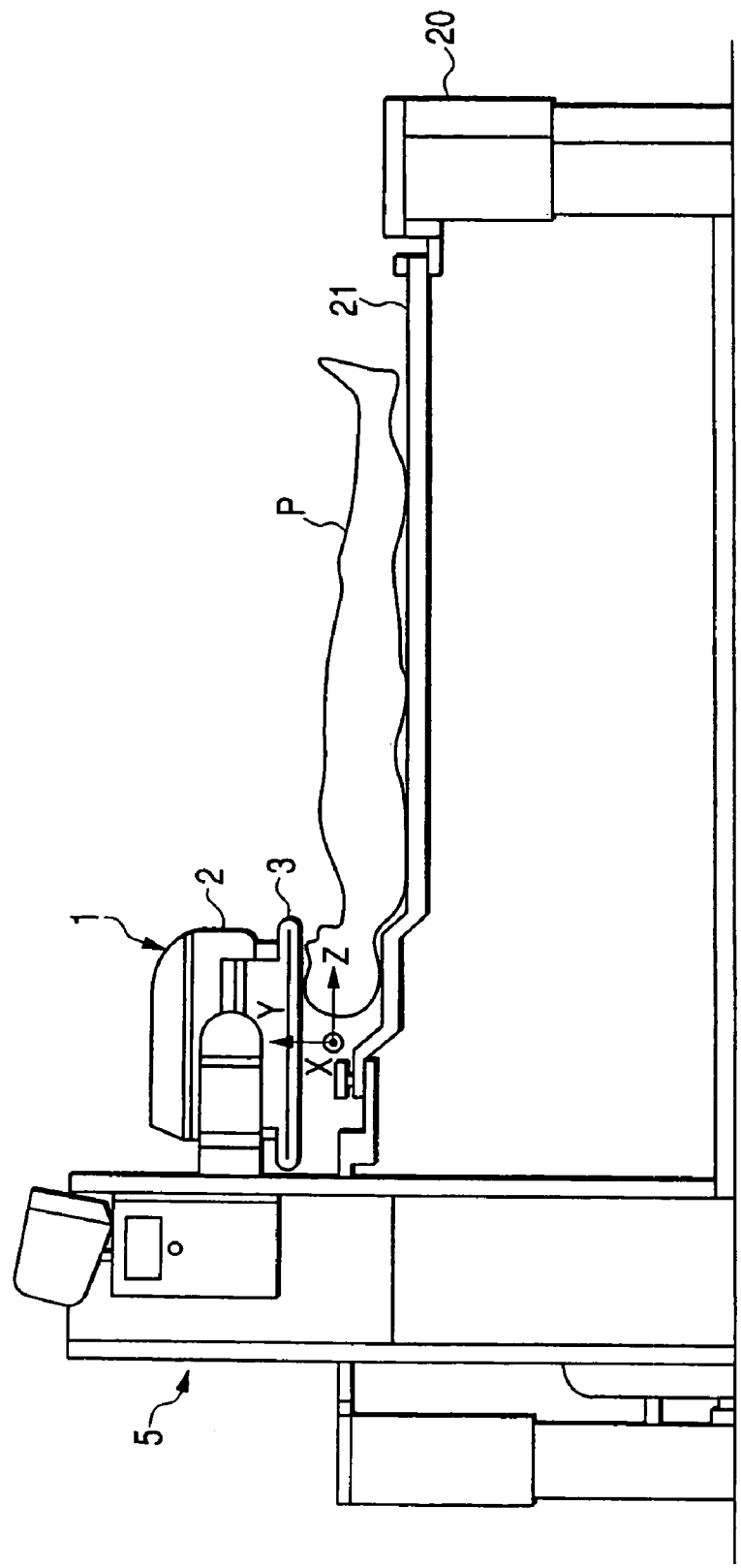
FIG. 2 is a diagram showing a gantry in FIG. 1.

As shown in FIGS. 1 and 2, the SPECT apparatus in this embodiment includes a gamma ray detector apparatus 1 and a gantry 5 for supporting the detector apparatus 1 to freely rotate around a rotation axis (a Z axis) substantially coinciding with an axis of a patient P mounted on a top board 21 of a bed 20. A rotation coordinate system rotating around the Z axis is defined. In the rotation coordinate system, a direction axis perpendicular to a detection surface of a detector 2 is set as a Y axis and a channel direction axis of the detector 2 is set as an X axis.

The detector apparatus 1 includes the two-dimensional detector 2 and a parallel hole collimator 3. The detector 2 performs two-dimensional position detection using a two-dimensional (plane) scintillator and plural photomultiplier tubes. NaI (Tl) or the like is used for the scintillator. The parallel hole collimator 3 is constituted by a lead plate with plural holes drilled in parallel in order to limit an angle of incidence of gamma rays reaching the detector 2 from radiation sources (RIs).

The gantry 5 is controlled by a gantry control unit 6 to rotate the detector apparatus 1. In performing imaging, an imaging control unit 7 controls the gantry control unit 6 such that the detector apparatus 1 intermittently (or continuously) rotates at a fixed period around the patient P. A collecting unit 4 reads out a signal charge from the detector 2 and digitizes the signal charge. In addition, the collecting unit 4 discriminates events (gamma ray incidence events) in an energy window corresponding to dosed RIs and aggregates, for each stop period of the detector apparatus 1, the number of events put in the energy window for each incidence position of a gamma ray. As a result of aggregation of each cell, the number of RIs is accumulated substantially along the Y axis. As a result of aggregation, a two-dimensional spatial distribution (a two-dimensional projection distribution) of the number of RIs, which is a distribution obtained by projecting a three-dimensional RI distribution on a detector surface substantially along the Y axis, is acquired for each projection angle. Data of plural two-dimensional projection distributions with different projection angles is stored in an image storing unit 9 in association with an angle (a projection angle) of the detector 2.

The imaging control unit 7 and the image storing unit 9 constitute a console box together with an input unit 11 such as a keyboard and a mouse, a control unit 8, and an image processing unit 12. The image processing unit 12 has a function of reconfiguring a three-dimensional RI distribution from plural two-dimensional projection distributions with different projection angles and correcting, in order to reduce a fall in spatial resolution according to distances between RIs and the detector 2, the plural two-dimensional projection distribution with different projection angles detected by the detector 2 according to plural correction functions corresponding to the distances on a three-dimensional frequency space. Therefore, the image processing unit 12 includes a three-dimensional filter storing unit 13, a sinogram transforming unit 14, a filter processing unit 15, a Fourier transformation unit 16, an inverse Fourier transformation unit 17, and a reconfiguration processing unit 18.

The three-dimensional filter storing unit 13 stores data of plural filter functions (correction functions) corresponding to the plural distances, respectively. The sinogram transforming unit 14 transforms plural two-dimensional projection distributions (XZ surface distributions) with different projection angles into a three-dimensional projection distribution (a three-dimensional sinogram) represented by a three-dimensional actual space formed by a projection angle axis (a $\phi$ axis), a slice axis (a Z axis), and a channel axis (an X axis). The Fourier transformation unit 16 transforms the three-dimensional sinogram into a representation ($\gamma$, n, w) in a frequency space from a representation (X, $\phi$, Z) in the actual space. $\gamma$ is a frequency equivalent to a channel direction X in the actual space, n is a frequency equivalent to a projection angle $\phi$ in the actual space, w is a frequency equivalent to a slice axis direction Z in the actual space.

The filter processing unit 15 corrects spatial resolution by using the plural filter functions (correction functions) stored in the three-dimensional filter storing unit 13 properly and convoluting the filer functions with respect to the three-dimensional sinogram represented in the frequency space. As described above, a degree of a fall in spatial resolution changes according to the radiation source to detector distances d. Since the distances d cannot be separated on the actual space, the fall in spatial resolution cannot be corrected effectively. However, it is possible to separate the distances d and correct the fall in spatial resolution by shifting the three-dimensional sinogram to the frequency space. The inverse Fourier transformation unit 17 transforms (returns) the three-dimensional sinogram subjected to the correction of spatial resolution into a representation in the actual space from the representation in the frequency space. The reconfiguration processing unit 18 reconfigures a three-dimensional RI distribution from the three-dimensional sinogram returned to the representation in the actual space subjected to the correction of spatial resolution.

Figure 4:
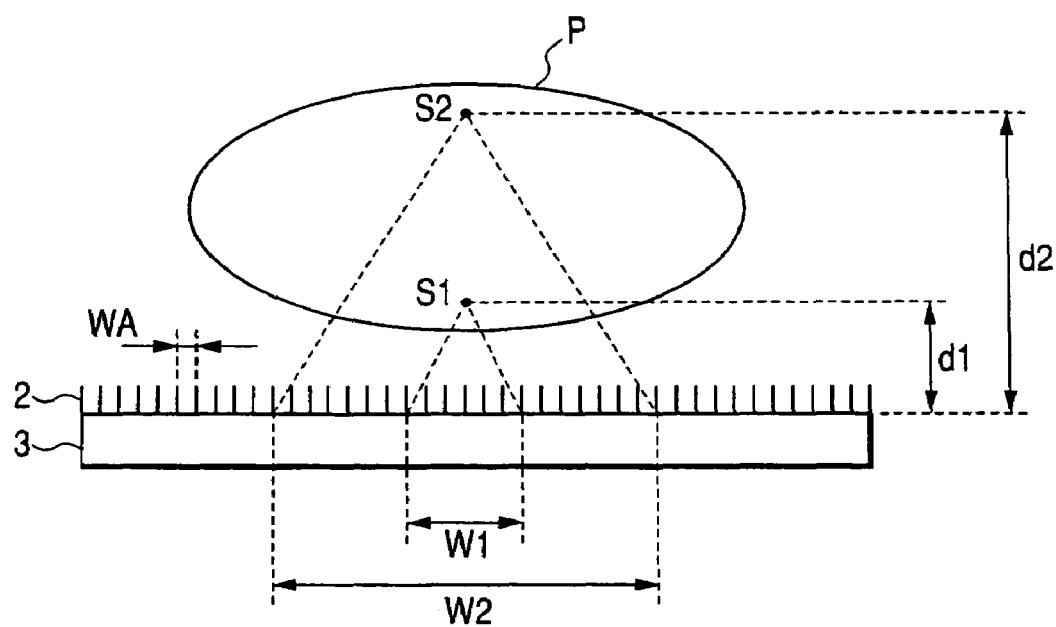
FIG. 4 is a diagram for explaining a relation between radiation source to detector distances d and a degree of unsharpness in step S22 in FIG. 3.

A principle of occurrence of the fall in spatial resolution is shown in FIG. 4. RIs dosed to the patient P gather in target regions. Positions of the RIs are assumed to be S1 and S2. The radiation source position S1 is apart from the detection surface of the detector 2 by a distance d1. The radiation source position S2 is apart from the detection surface of the detector 2 by a distance d2 larger than the distance d1 of the radiation source position S1. Each hole of the collimator 3 has an opening width WA. Therefore, a gamma ray radiated from the radiation source position S1 reaches the detection surface of the detector 2 in a range of a width W1. A gamma ray radiated from the radiation source position S2 is made incident on the detection surface of the detector 2 in a range of a width W2 larger than the width W1. Spatial resolution increases but sensitivity falls as an incidence width is smaller. Conversely, sensitivity increases but spatial resolution falls as an incidence width is larger. The opening width WA is designed based on sensitivity and spatial resolution that are in a trade-off relation. Therefore, it is inevitable to give a certain degree of the opening width WA to the collimator 3.

Figure 5C:
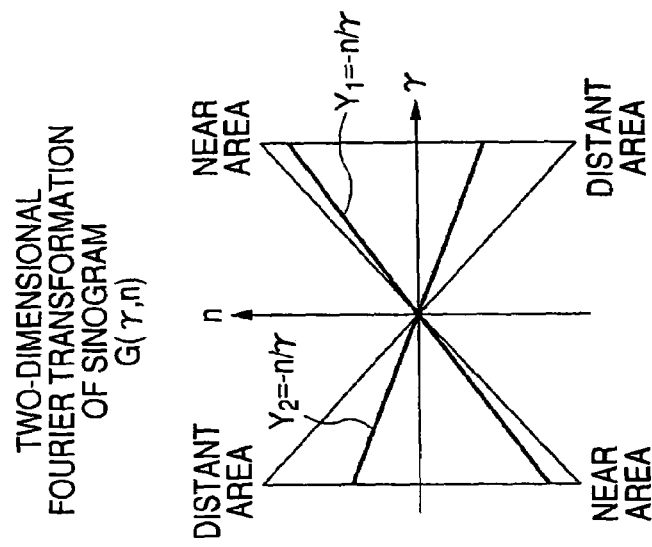
FIG. 5C is a diagram showing the sinogram in FIG. 5B on a frequency space through two-dimensional Fourier transformation.
Figure 5B:
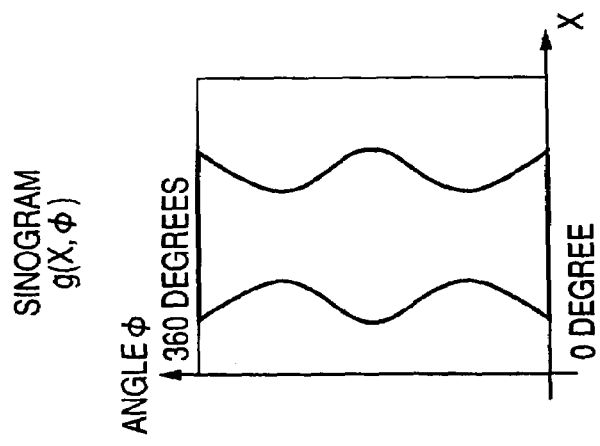
FIG. 5B is a diagram showing a two-dimensional sinogram corresponding to FIG. 5A.
Figure 5A:
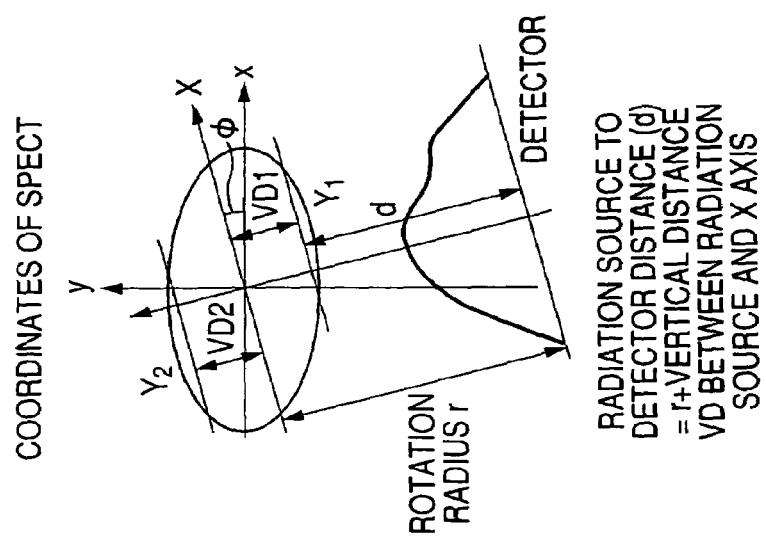
FIG. 5A is a diagram showing a two-dimensional SPECT coordinate system for supplementing the explanation of the correction processing for a fall in spatial resolution (unsharpness) according to the embodiment.

As a method of correcting such a fall in spatial resolution due to an opening width of the collimator 3 according to filter processing, a Frequency Distance Relation (FDR) method is adopted. First, a principle of this FDR method is explained in an example of a two-dimensional space. Assuming that X is a detection position and $\phi$ is an angle (a projection angle) of the detector 2, when two-dimensional Fourier transformation is applied to two axis of X and $\phi$, G($\gamma$,n) shown in FIG. 5C is obtained with respect to a sinogram g(X,$\phi$) shown in FIG. 5B that is obtained by expanding a one-dimensional projection distribution concerning a detection position X shown in FIG. 5A along an axis of a projection angle $\phi$. $\gamma$ represents a frequency component of a detection position and n represents a frequency component of a detector (projection) angle. In other words, plural one-dimensional projection distributions with different projection angles are transformed from a representation on the actual space into a representation on the frequency space. Note that a projection distribution of RIs represented on the frequency space is referred to as an FDR image.

On the frequency space, data with the same distances d between a radiation source and a detector are present on a straight line Y=$-$n/$\gamma$ in an FDR image G($\gamma$,n). Y represents a distance between a line parallel to the detector 2 and including a rotation center and the radiation source. A fall in spatial resolution in the SPECT depends on openings of the collimator 3. The fall in spatial resolution due to the collimator openings depends on a distance between the radiation source and the detector 2 (= the collimator). Thus, the data on the straight line Y=−n/γ in G (γ, n) is subjected to a fall in spatial resolution of the same degree. It is possible to separate the distances d on the frequency space. It is possible to represent the fall in spatial resolution due to the collimator openings with, for example, the Gaussian function. Thus, as indicated by the following expressions, it is possible to correct the fall in spatial resolution due to the collimator openings by multiplying each data on the straight line Y=−n/γ in G(γ,n) by an inverse function (a correction function) provided for each of the distances d. F(γ,n) represents an ideal FDR image without a fall in spatial resolution. H(γ,n) represents a line spread function (an unsharpness function (see FIG. 6A)) represented on the frequency space.

$$G(\gamma,n)=H(\gamma,n)\times F(\gamma,n)$$

$$F(\gamma,n)=H-1(\gamma,n)\times G(\gamma,n)$$

Note that, concerning the inverse function, since an infinitely high high-frequency component is restored if a logical form is used, it is difficult to apply the inverse function in a practical use. Thus, a Metz filter (P=3, 5, or 7) or the like obtained by properly cutting a high-frequency component from a filter function of P=∞ is used (see FIG. 6B).

Figure 3:
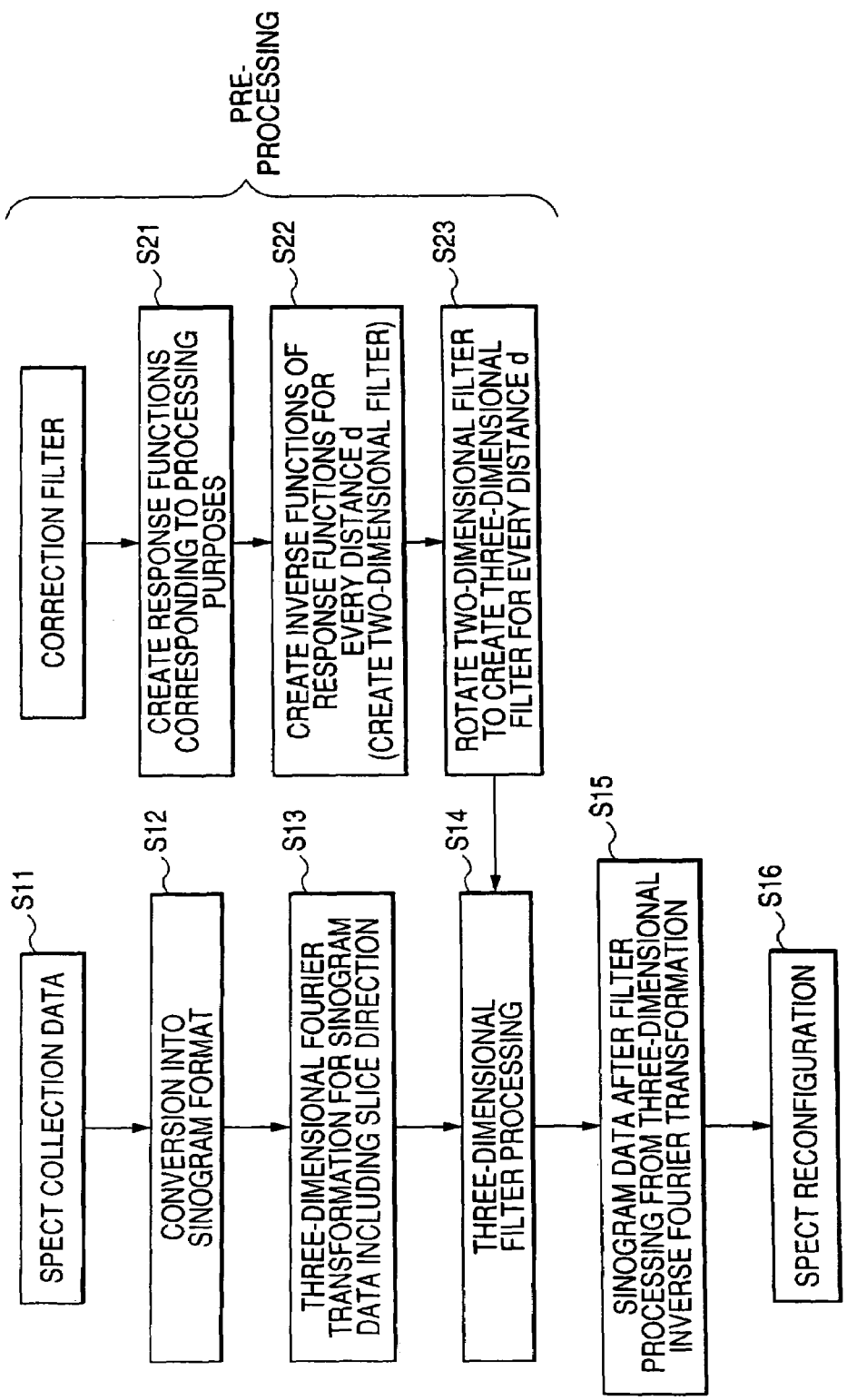
FIG. 3 is a flowchart of unsharpness correction processing according to the embodiment.
Figure 8A:
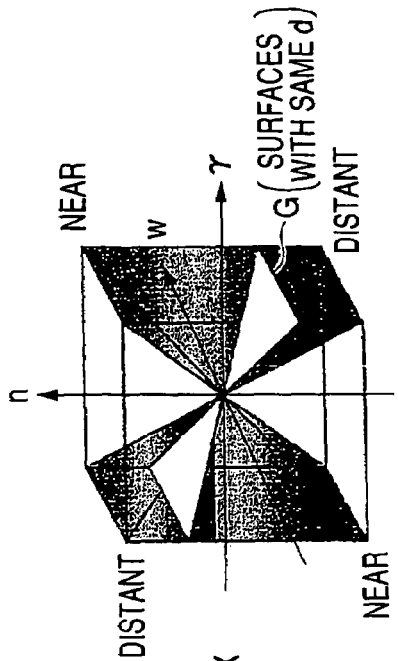
FIG. 8A is a diagram showing a three-dimensional SPECT coordinate system for supplementing the explanation of the correction processing for a fall in spatial resolution (unsharpness) according to the embodiment.
Figure 8B:
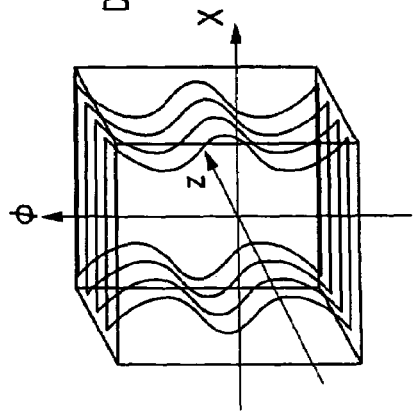
FIG. 8B is a diagram showing a three-dimensional sinogram corresponding to FIG. 8A.
Figure 8C:
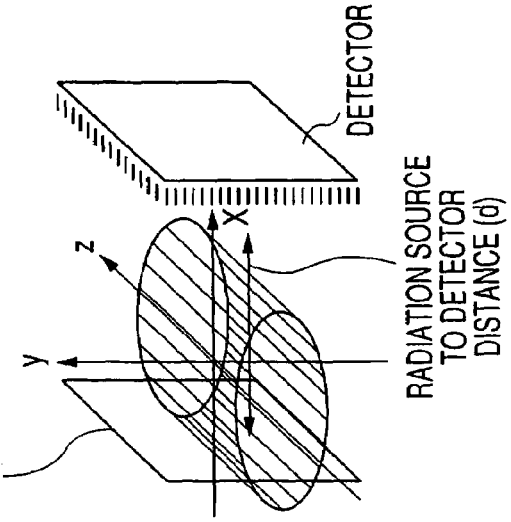
FIG. 8C is a diagram showing the sinogram in FIG. 8B on a frequency space through a three-dimensional Fourier transformation.

The three-dimensional filter processing in the SPEC apparatus in this embodiment is executed using the FDR filter processing. Procedures for the correction processing for a fall in spatial resolution (unsharpness) according to this embodiment are shown in FIG. 3. Imaging (counting) is repeated in plural positions while the detector apparatus 1 intermittently or continuously rotates around the patient P (S11). Collected SPECT data is stored in the image storing unit 9. As shown in FIG. 8A, the sinogram transforming unit 14 expands a one-dimensional projection distribution concerning a detection position X along an axis of a projection angle φ and transforms the one-dimensional projection distribution into a three-dimensional sinogram g(X,φ,Z) shown in FIG. 8B arranged for each slice (S12). The Fourier transformation unit 16 subjects the three-dimensional sinogram g(X,φ,Z) to three-dimensional Fourier transformation concerning three axes X, φ, Z (S13) to obtain a three-dimensional sinogram G(γ,n,w) shown in FIG. 8C represented on a frequency space. γ represents a frequency component in a detection position, n represents a frequency component of an angle (a projection angle) of the detector 3, and w represents a frequency component in a slice direction.

The filter processing unit 15 convolutes a correction function for each of the distances d with respect to the three-dimensional sinogram G(γ,n,w) represented on the frequency space (S14). Design of a filter for correcting the fall in spatial resolution due to the collimator openings is described. First, two-dimensionally, in a (γ,n) surface of G(γ,n,w), a filter is designed for each straight line Y=−n/γ on the basis of a logic of FDR.

Figure 6A:
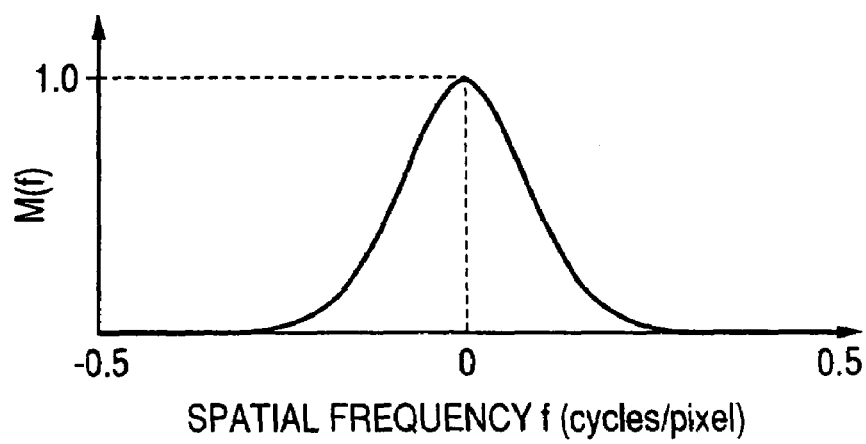
FIG. 6A is a diagram showing a one-dimensional distribution (a line spread function) of unsharpness in the embodiment.
Figure 6B:
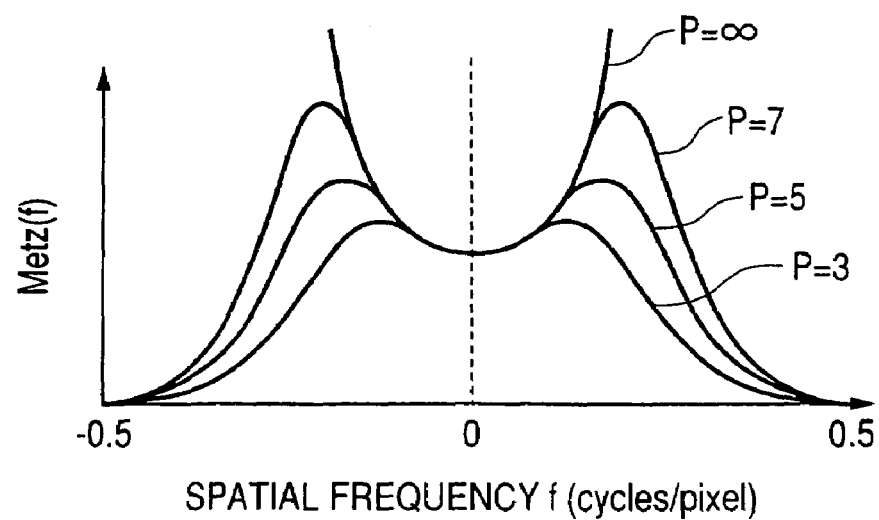
FIG. 6B is a diagram showing an inverse function of the line spread function in FIG. 6A.

For example, a spatial resolution depending on a distance between a collimator and a radiation source is represented by a mountain-like shape shown in FIG. 6A. A shape of this point spread function can be approximated by the Gaussian distribution, the Poisson distribution, or the like. As the point spread function, a Modulation Transfer Function (MTF) is adopted. The MTF is represented by the following expression.

$$M(f)=e^q$$

$$q=-2\pi^2\sigma^2 f^2$$

A position resolution is reflected in a half-value breadth. This distribution is created for each of the distances d between the collimator and the radiation source and set as a response function (S21). An inverse function of the response function created for each of the distances d is created (S22). In other words, a two-dimensional filter is created for each of the distances d. Note that, since the inverse function may diverge at a high frequency, a high-frequency component is cut to a degree not intensifying noise. For example, the inverse function has a shape like a Metz filter shown in FIG. 6B. The Metz filter is represented by the following expression. Note that P is a statistical fluctuation control parameter serving as a parameter determining a filter characteristic. When P increases, the Metz filter has a higher correction effect but is sensitive to noise. When P decreases, the Metz filter has a lower correction effect but has stronger resistance against noise.

$$Metz(f)=\{1-(1-M(f)^2)^P\}/M(f)$$

Expansion to three dimensions including the slice direction only has to be performed by rotating the correction filter obtained two-dimensionally because data with the same radiation source to detector (collimator) distances including the slice direction are present on a surface including the straight line Y=−n/γ and a straight line of a w axis (S23). Actually, to expand a filtering object from two dimensions to three dimensions, the filter is expanded from one dimension to two dimensions. Specifically, a point spread function shown in FIG. 7A can be expanded to a two-dimensional distribution shown in FIG. 7B by rotating the point spread function conically around an axis passing through an origin (a frequency=0) of an abscissa. As shown in FIG. 9, G(γ,n,w) is corrected by a three-dimensional correction filter serving as an inverse function of a two-dimensional point spread function designed for each surface including the straight line Y−n/γ and the straight line of the w axis. The three-dimensional correction filter is convoluted with respect to respective local areas with respective points of G(γ,n,w) as centers. The three-dimensional correction filter is properly used according to the distances d. Consequently, it is possible to properly correct a fall in spatial resolution according to the distances d. The inverse function of the two-dimensional point spread function, that is, a filter function is created for each of the distances d in advance. Plural filter functions are stored in the storing unit 13 in association with the distances d.

Note that, as described above, the filter function has the statistical fluctuation control parameter P. It is effective to properly use plural kinds of filter functions with different parameters P according to a noise level of collected data. When P increases, the filter function has a higher correction effect but is sensitive to noise. When P decreases, the filter function has a lower correction effect but has stronger resistance against noise.

Therefore, the plural kinds of filter functions with different parameters P are created in advance. The plural kinds of filter functions with different parameters P are stored in the storing unit 13 together with the distances d in association with the parameters P. The filter processing unit 15 can properly use the filter functions according to the distances d and the parameters P. Typically, an amount of RIs that can be dosed in a patient is substantially determined according to a physique (weight, height, etc.) of the patient, a test region, and a type of a drug marked by the RIs. When a dosage of the RIs is large, noise is small. Conversely, when a dosage of the RIs is small, noise is large. The filter processing unit 15 can select an optimum filter function in accordance with the dosage of the RIs and the test region and the like determining the dosage. A filter function satisfying a condition, with which an influence of noise is not made manifest, and having a highest correction effect, that is, a highest parameter P corresponds to the optimum filter function.

The filter processing unit 15 corrects plural two-dimensional projection distributions (a three-dimensional sinogram) initially using the optimum filter function selected in accordance with the dosage of the RIs and the test region and the like determining the dosage. A three-dimensional RI distribution is reconfigured and displayed on the basis of the corrected three-dimensional sinogram.

Note that the filter processing unit 15 may correct three-dimensional sinograms initially using all the filter functions with different filter characteristics, that is, different statistical fluctuation control parameters P in this embodiment, respectively. In this case, on the basis of the corrected plural three-dimensional sinograms, RI distributions with different filter characteristics corresponding to the three-dimensional sinograms are reconfigured by the reconfiguration processing unit 18. The plural three-dimensional RI distributions are displayed in a display unit 10 as a list.

The inverse Fourier transformation unit 17 returns $G(\gamma,n,w)$, which has the fall of spatial resolution corrected, to the three-dimensional sinogram $g(X,\phi,Z)$ represented on the actual space according to the inverse Fourier transformation (S15). The reconfiguration processing unit 18 reconfigures a SPECT tomogram with a multi-stage surface from the three-dimensional sinogram $g(X,\phi,Z)$ that has the fall in spatial resolution corrected and is returned to the representation on the actual space (S16).

According to this embodiment, it is possible to separate the radiation source to detector distances d by transforming a two-dimensional projection distribution in multiple directions into a three-dimensional sinogram and transferring the three-dimensional sinogram to a frequency space. Thus, it is possible to effectively correct a fall in spatial resolution with an appropriate correction function according to the distances d.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A SPECT apparatus comprising:
a two-dimensional detector that detects radiations from RIs in a patient via a collimator;
a correction processing unit that corrects, in order to reduce a fall in spatial resolution having dependency on distances between the respective RIs and the detector, plural two-dimensional projection distributions with different projection angles, which are detected by the detector, on a three-dimensional frequency space according to plural correction functions corresponding to plural distances, respectively; and
a reconfiguring unit that reconfigures a three dimensional RI distribution from the plural two-dimensional projection distributions corrected;
wherein the correction processing unit includes:
a coordinate transforming unit that transforms the plural two-dimensional projection distributions into a three-dimensional projection distribution represented by a three-dimensional actual space formed by a projection angle axis, a slice axis and a channel axis;
a transforming unit that transforms the three-dimensional projection distribution into a representation of a frequency space according to three-dimensional Fourier transformation;
a correcting unit that corrects values of respective points of the transformed three-dimensional projection distribution according to any one of the plural correction functions corresponding to distances of the respective points; and
a transforming unit that transforms the corrected three-dimensional projection distribution into a representation of the actual space according to the three-dimensional Fourier transformation.

2. A SPECT apparatus comprising:
a two-dimensional detector that detects radiations from RIs in a patient via a collimator;
a correction processing unit that corrects, in order to reduce a fall in spatial resolution having dependency on distances between the respective RIs and the detector, plural two-dimensional projection distributions with different projection angles, which are detected by the detector, on a three-dimensional frequency space according to plural correction functions corresponding to plural distances, respectively; and
a reconfiguring unit that reconfigures a three dimensional RI distribution from the plural two-dimensional projection distributions corrected;
wherein the correction function is an inverse function of a point spread function represented by the frequency space.

3. A SPECT apparatus according to claim 2, further comprising a storing unit that stores the plural correction functions.

4. A SPECT apparatus according to claim 2, wherein the point spread function is a modulation transfer function.

5. A SPECT apparatus according to claim 2, wherein the collimator is a parallel hole collimator.

6. A SPECT apparatus according to claim 2, further comprising a storing unit that stores data of the plural correction functions.

7. A SPECT apparatus according to claim 6, wherein the distances are associated with the data of each of the plural correction functions.

8. A SPECT apparatus according to claim 6, wherein parameters concerning the distances and filter characteristics are associated with the data of each of the plural correction functions.

9. A SPECT apparatus according to claim 8, wherein the reconfiguring unit reconfigures plural three-dimensional RI distributions on the basis of two-dimensional projection distributions corrected for each of the correction functions with the different filter characteristics.

10. A SPECT apparatus according to claim 9, further comprising a display unit that displays the plural three-dimensional RI distribution as a list.

11. A processing method for a SPECT comprising:
correcting plural two-dimensional projection distributions with different projection angles concerning RIs in a patient, which are detected by a two-dimensional detector, on a three-dimensional frequency space according to plural correction functions corresponding to plural distances between the RIs and the detector, respectively; and
reconfiguring a three-dimensional RI distribution from the plural two-dimensional projection distributions corrected;

wherein the correction function is an inverse function of a point spread function represented by the frequency space.

12. A processing method for a SPECT according to claim 11, wherein
in the correcting,
the plural two-dimensional projection distributions are transformed into a three-dimensional projection distribution represented by a three-dimensional actual space formed by a projection angle axis, a slice axis and a channel axis,
the three-dimensional projection distribution is transformed into representation of a frequency space according to three-dimensional Fourier transformation,
values of respective points of the transformed three-dimensional projection distribution are corrected according to any one of the plural correction functions corresponding to distances of the respective points, and
the corrected three-dimensional projection distribution is transformed into representation of the actual space according to the three-dimensional inverse Fourier transformation.

13. A processing method for a SPECT according to claim 11, wherein the point spread function is a modulation transfer function.

14. A program for SPECT processing for causing a computer to realize:
means for correcting plural two-dimensional projection distributions with different projection angles concerning RIs in a patient, which are detected by a two-dimensional detector, on a three-dimensional frequency space according to plural correction functions corresponding to plural distances between the RIs and the detector, respectively; and
means for reconfiguring a three-dimensional RI distribution from the plural two-dimensional projection distributions corrected;
wherein the correction function is an inverse function of a point spread function represented by the frequency space.

* * * * *

UNITED STATES PATENT AND TRADEMARK OFFICE
CERTIFICATE OF CORRECTION

PATENT NO. : 7,420,176 B2
APPLICATION NO. : 11/244283
DATED : September 2, 2008
INVENTOR(S) : Motomura et al.

It is certified that error appears in the above-identified patent and that said Letters Patent is hereby corrected as shown below:

On the title page, Item (73), the Assignee information is incorrect. Item (73) should read:

-- (73) Assignee: A School Juridical Person Fujita Educational Institution, Toyoake-shi (JP) --

Signed and Sealed this

Eleventh Day of November, 2008

JON W. DUDAS
*Director of the United States Patent and Trademark Office*